(12) United States Patent
Gustavsson et al.

(10) Patent No.: US 9,138,435 B2
(45) Date of Patent: Sep. 22, 2015

(54) REDUCTION OF TOXICITY OF MULTI-TARGETING ANTIFOLATES

(75) Inventors: Bengt Gustavsson, Västra Frölunda (SE); Göran Carlsson, Jonsered (SE)

(73) Assignee: ISOFOL MEDICAL AB, Gothenburg (SE)

(*) Notice: Subject to any disclaimer, the term of this patent is extended or adjusted under 35 U.S.C. 154(b) by 230 days.

(21) Appl. No.: 12/805,287

(22) Filed: Jul. 22, 2010

(65) Prior Publication Data

US 2010/0311762 A1 Dec. 9, 2010

Related U.S. Application Data

(63) Continuation of application No. 10/583,508, filed as application No. PCT/SE2004/001955 on Dec. 22, 2004, now abandoned.

(30) Foreign Application Priority Data

Dec. 22, 2003 (SE) ........................... 0303526

(51) Int. Cl.
*A61K 31/519* (2006.01)
(52) U.S. Cl.
CPC .................................... *A61K 31/519* (2013.01)
(58) Field of Classification Search
None
See application file for complete search history.

(56) References Cited

U.S. PATENT DOCUMENTS

| 5,376,658 | A | | 12/1994 | Spears | |
|---|---|---|---|---|---|
| 6,011,040 | A | * | 1/2000 | Muller et al. | 514/250 |
| 6,921,667 | B2 | * | 7/2005 | Dervieux et al. | 436/63 |

FOREIGN PATENT DOCUMENTS

WO  WO 9117660  11/1991

OTHER PUBLICATIONS

"Folate Status and the Safety Profile of Antifolates". Hilary Calvert. Seminars in Oncology, vol. 29, No. 2, Suppl 5, pp. 3-7 (Apr. 2002).
"Homocysteine and Methylmalonic Acid: Markers to Predict and Avoid Toxicity from Pemetrexed Therapy". Clet Niyikiza et al. Molecular Cancer Therapeutics, vol. 1, pp. 545-552 (May 2002).
"Role of Folic Acid in Modulating the Toxicity and Efficacy of the Multitargeted Antifolate, LY231514". John F. Worzalla et al. Anticancer Research, vol. 18, pp. 3235-3240 (1998).
European Office Action dated Jul. 29, 2008 in corresponding European Application No. 04 809 128.4-2123.
Roberts et al.; "Weekly lometrexol with daily oral folic acid is appropriate for phase II evaluation", Cancer Chemother Pharmacol (2000) 45: 103-110.
Curtin et al., "Pemetrexed disodium, a novel antifolate with multiple targets", The Lancet Oncology, vol. 2, May 2001, pp. 298-306.

Hanauske et al. The Oncologist, 2001, vol. 6, pp. 363-373.
Thomas Purcell W et al; "Novel Antifolate Drugs", Evolving Therapies, pp. 114-125, Mar. 2003.
Scagliotti, Giorgio V et al; Phase II Study of Pemetrexed With and Without Folic Acid and Vitamin B12 as Front-Line Therapy in Malignant Pleural Mesothelioma, Journal of Clinical Oncology, vol. 21, No. 8, Apr. 15, 2003, pp. 1556-1561.
Banerjee D et al; "Novel aspects of resistance to drugs targeted to dihydrofolate reductase and thymidylate synthase", Biochimica et Biophysica Acta 1587 (2002) 164-173.
Kelly GS, "Folates: supplemental forms and therapeutic applications"; Altem Med Rev 1998; 3:208-20.
Devlin AM et al, "Glutamate carboxypeptidase II: a polymorphism associated with lower levels of serum folate and hyperhomocysteinemia"; Hum Mol Genet 2000;9:2837-44.
Sirotnak FM, Tolner B, "Carrier-mediated membrane transport of folates in mammalian cells"; Annu Rev Nutr 1999; 19:91-122.
Shane B, "Folylpolyglutamate synthesis and role in the regulation of one-carbon metabolism"; Vitam Horm 1989; 45:263-335.
Spears CP et al, "Deoxyuridylate effects on thymidylate synthase-5-fluorodeoxyuridylate- folate ternary complex formation"; Biochem Pharmacol 1989; 38:2985-93.
Spears CP, et al "Thymidylate synthetase inhibition in malignant tumors and normal liver of patients given intravenous 5-fluorouracil", Cancer Res 1984; 44:4144-50.
Galivan J et al, "Glutamyl hydrolase. pharmacological role and enzymatic characterization", Pharmacol Ther 2000; 85:207-15.
Costi MP, Ferrari S, "Update on antifolate drugs targets"; Curr Drug Targets 2001; 2:135-66.
Cohen V et al, "Methylenetetrahydrofolate Reductase Polymorphism in Advanced Colorectal Cancer: A Novel Genomic Predictor of Clinical Response to Fluoropyrimidine-based Chemotherapy"; Clin Cancer Res 2003; 9:1611-5.
Stevenson JP et al "Phase I clinical and pharmacogenetic trial of irinotecan and raltitrexed administered every 21 days to patients with cancer"; J Clin Oncol 2001; 19:4081-7.
Guinotte CL et al "Methylenetetrahydrofolate reductase 677C-->T variant modulates folate status response to controlled folate intakes in young women"; J Nutr 2003; 133:1272-80.
De Cabo SF et al, "Molecular and cytological evidence of S-adenosyl-L-homocysteine as an innocuous undermethylating agent in vivo"; Cytogenet Cell Genet 1995; 71:187-92.

(Continued)

*Primary Examiner* — James D Anderson
(74) *Attorney, Agent, or Firm* — Harness, Dickey & Pierce, P.L.C.

(57) ABSTRACT

The use of tetrahydrofolate, methylene-tetrahydrofolate and/or methyl-tetrahydrofolate, and at least one multi-targeting antifolate, for the manufacture of a pharmaceutical composition for the treatment of cancer is disclosed. By combining the multi-targeting antifolate with tetrahydrofolate, methylene-tetrahydrofolate and/or methyl-tetrahydrofolate, it is possible to remarkably reduce toxic side-effects without diminishing the anti-tumor action of the drugs. A pharmaceutical composition, a kit comprising the pharmaceutical composition as well as a method for the treatment of cancer are also disclosed.

16 Claims, 5 Drawing Sheets

(56) References Cited

OTHER PUBLICATIONS

Stoehlmacher J et al, "A polymorphism of the XRCC1 gene predicts for response to platinum based treatment in advanced colorectal cancer" Anticancer Res 2001; 21:3075-9.

Kim et al; "Colonic mucosal concentrations of folate correlate well with blood measurements of folate status in persons with colorectal polyps", Am J Clin Nutr 1998; 68: 866-72.

Hanauske A, et al "Pemetrexed Disodium: A Novel Antifolate Clinically Active Against Multiple Solid Tumors", The Oncologist, 6:363-373 (2001).

Jackman AL et al in "ICI D1694, a quinazoline antifolate thymidylate synthase inhibitor that is a potent inhibitor of L1210 tumor cell growth in vitro and in vivo: a new agent for clinical study", Cancer Res Oct. 15, 1991; 51(20):5579-86.

Raghunathan K et al "Impact of schedule on leucovorin potentiation of fluorouracil antitumor activity in dietary folic acid deplete mice"; Biochem Pharmacol 1997; 53:1197-202.

International Search Report dated Apr. 18, 2005 issued in PCT/SE2004/001955.

Shih, C., et al., (1997), "LY231514, a Pyrrolo[2,3-d]pyrimidine-based antifolate that inhibits multiple folate-requiring enzymes", *Cancer Research*, 57: 1116-1123.

\* cited by examiner

REDUCTION OF TOXICITY OF MULTI-TARGETING ANTIFOLATES

CROSS-REFERENCE TO RELATED APPLICATIONS

This application is a continuation of and claims priority under 35 U.S.C. §120 on U.S. patent application Ser. No. 10/583,508 filed on May 15, 2007 now abandoned, which is a National Phase of PCT Patent Application No. PCT/SE2004/001955, filed on Dec. 22, 2004, which claims priority under 35 U.S.C. §119 to Sweden Patent Application No. 0303526-8, filed on Dec. 22, 2003, the contents of each of which are hereby incorporated by reference in their entirety.

TECHNICAL FIELD

The present invention relates to the use of multi-targeting antifolates for the manufacture of a pharmaceutical composition for the treatment of cancer.

BACKGROUND ART

The control of drug-related toxicity (e.g. myelosuppression, diarrhea, mucosal toxicity, and infection) has been a major concern throughout the history of cancer chemotherapy. Substances conventionally used in cancer chemotherapy are e.g. antifolates, anthracyclines, and antineoplastic agents.

Antifolates, or folate antagonists, constitute a class of antimetabolites, and are active chemotherapeutic agents for many solid tumor and hematologic malignancies (Thomas Purcell W et al; "Novel Antifolate Drugs", Evolving Therapies, pp 114-125, March 2003).

For many years, methotrexate (MTX) has been the major antifolate antimetabolic agent used in clinical medicine. The primary cellular target of MTX is the enzyme dihydrofolate reductase (DHFR) and thus, MTX is a single enzyme targeting antifolate. There are also other approved agents which only attack single enzyme targets, e.g. 5-fluorouracil (5-FU), which inhibit thymidylate synthase (TS) (Scagliotti, Giorgio V et al; Phase II Study of Pemetrexed With and Without Folic Acid and Vitamin B12 as Front-Line Therapy in Malignant Pleural Mesothelioma", Journal of Clinical Oncology, Vol 21, No 8, Apr. 15, 2003, pp 1556-1561).

Although response to treatment is observed in patients, many of them relapse due to development of resistance. Drug resistance is often a limiting factor in successful chemotherapy with single enzyme targeting antifolates (Banerjee D et al; "Novel aspects of resistance to drugs targeted to dihydrofolate reductase and thymidylate synthase", Biochimica et Biophysica Acta 1587 (2002) 164-173).

Novel antifolates have been developed to improve the efficacy and toxicity profile or to decrease the various known mechanisms of resistance to antifolate therapy.
These novel antifolates are multi-targeting antifolates that have demonstrated broad-spectrum antitumor activity. This new generation of antifolates inhibits several key folate-requiring enzymes of the thymidine and purine biosynthetic pathways, in particular thymidylate synthase, DHFR and GARFT (glycinamide ribonucleotide formyltransferase), by competing with reduced folates for binding sites. The consequent inhibition of intracellular folate metabolism leads to the inhibition of cell growth (Niyikiza C et al; "Homocysteine and Methylmalonic Acid: Markers to Predict and Avoid Toxicity from Pemetrexed Therapy", Molecular Cancer Therapeutics, Vol 1, 545-552, May 2002).

The cytotoxic activity and subsequent effectiveness of antifolates can be associated with substantial toxicity for some patients. Antifolates, as a class, have been associated with sporadic severe myelosuppression with gastrointestinal toxicity. A combination of such toxicities can carry a high risk of mortality. The inability to control these toxicities has led to the discontinuation of clinical development of some antifolates, and complicated the clinical development of others (Niyikiza C let et al; "Homocysteine and Methylmalonic Acid Markers to Predict and Avoid Toxicity from Pemetrexed Therapy", Molecular Cancer Therapeutics, Vol 1, 545-552, May 2002).

U.S. Pat. No. 5,376,658 (Spears et al) discloses the use of $CF_2FH_4$, and its solution product isomer $FH_4$, as a modulator of 5-FU in cancer chemotherapy. Also disclosed is a method of using $CF_2FH_4$ or $FH_4$ in order to reduce the toxicity of an anti-folate drug which has been administered to a patient. The anti-folate drugs disclosed are methotrexate, trimetrexate, nitrous oxide, and dideoxytetrahydrofolic acid, all of which belong to the group of single enzyme targeting antifolates.

Treatment with specific TS inhibitors like 5-FU in combination with folinic acid has been shown to reduce side-effects without reducing tumor effect. It seems that folate deficiency may have contributed to the toxicity in some cancer patients, and nutritional supplementation with folic or folinic acid had led to a reduction in toxicity and treatment-related deaths with preservation of anticancer activity (Calvert H; "Folate status and the safety profile of antifolates"; Semin Oncol 2002; 29:3-7).

In a recent study, Niyikiza et al reported that supplementation with folic acid may lead to a better safety profile in patients treated with pemetrexed, and possibly to an improved efficacy. Toxicity could be modulated by folic acid supplementation, and the maximum tolerated dose could be increased (Niyikiza C et al, "Homocysteine and methylmalonic acid: markers to predict and avoid toxicity from pemetrexed therapy"; Mol Cancer Ther 2002; 1:545-52).

However, the metabolism of folic acid is a very complex process, and many metabolic steps are required in order to achieve the active substances of the folic acid metabolism. Folic acid is the most oxidized and stable form of folate and must be deconjugated, reduced, and methylated to be metabolically active in the cell (Kelly G S, "Folates: supplemental forms and therapeutic applications"; Altern Med Rev 1998; 3:208-20).

Folic acid supplementation to reduce toxicity is thus actually quite inefficient, and may additionally lead to unwanted metabolic intermediates. Until now, no satisfactory way of reducing the toxicity of multi-targeting antifolates has been proposed. Considering the very promising action of antifolates, a possibility to efficiently reduce their side effects is very much sought-after. There is thus a need for a way of reducing toxicity, and at the same time maintaining or improving the efficiency of multi-targeting antifolates, in order to be able to use them efficiently in clinic.

SUMMARY OF THE INVENTION

An aim of the present invention is to overcome the above-mentioned drawbacks and provide an improved way of reducing the toxicity, and maintaining or improving the efficiency, of multi-targeting antifolates.

This aim is achieved by the use of tetrahydrofolate (THF), methylene-tetrahydrofolate (methylene-THF) and/or methyl-tetrahydrofolate (methyl-THF), and at least one multi-targeting antifolate, for the manufacture of a pharmaceutical composition for the treatment of cancer.

The use of THF, methylene-THF and/or methyl-THF in combination with a multi-targeting antifolate according to the present invention dramatically reduces the side effects of multi-targeting antifolates and, consequently, the therapeutic index is improved. It is thus possible to administer a higher dose to the tumor without increasing the side-effects, which leads to a better clinical effect.

Preferably, at least 60% by weight of said THF, methyl-THF and/or methylene-THF is in the form of a biologically active isomer. Thereby, the synergistic effects of the combination with multi-targeting antifolates are optimised.

Said multi-targeting antifolate may be selected from the group consisting of pemetrexed, raltitrexed, and lometrexol. However, also other multi-targeting antifolates, as well as other substances which possess the characteristics of multi-targeting antifolates may be used.

The pharmaceutical composition may further comprise at least one chemotheropeutic agent selected from the group consisting of anthracyclines, platinum derivatives, topoisomerase inhibitors, and antimetabolites. The reduction of severe side-effects obtained by the present invention provides for greater combination possibilities.

Said anthracycline may be selected from the group consisting of doxorubicin and epirubicin; said platinum derivative may be selected from the group consisting of oxaliplatin, cisplatin, and carboplatin; said topoisomerase inhibitor may be selected from the group consisting of irinotecan and CPT11 (a topoisomerase I-inhibitor); and said antimetabolite may be selected from the group consisting of capecitabine, gemcitabin, UFT and S1. However, also other substances belonging to the aforementioned groups of substances may be used.

The THF, methylene-THF and/or methyl-THF, and said multi-targeting antifolate, may be formulated in different pharmaceutical compositions, or in a common pharmaceutical composition. The formulation into different compositions provides for a great administration flexibility. The formulation into a common pharmaceutical composition, on the other hand, provides for a simple manufacturing process, as well as for a simple way of administration.

Examples of cancers to be treated according to the invention are breast cancer, gastric cancer, gall bladder cancer, bile duct cancer, colon cancer, rectal cancer, liver cancer, pancreatic cancer, head and neck cancer, and mesotheolioma cancer.

The present invention also relates to a pharmaceutical composition comprising at least one multi-targeting antifolate and THF, methylene-THF and/or methyl-THF. Preferably, at least 60% by weight of said THF, methyl-THF and/or methylene-THF is in the form of a biologically active isomer. The pharmaceutical composition may further comprise at least one chemotherapeutic agent selected from the group consisting of anthracyclines, platinum derivatives, topoisomerase inhibitors, and antimetabolites.

Further, the present invention relates to a kit comprising a pharmaceutical composition comprising at least one multi-targeting antifolate and a pharmaceutical composition comprising THF, methylene-THF and/or methyl-THF or isomers thereof. Preferably, at least 60% by weight of said THF, methyl-THF and/or methylene-THF is in the form of a biologically active isomer. Such a kit may further comprise a pharmaceutical composition comprising a chemotherapeutic agent selected from the group consisting of, anthracyclines, platinum derivatives, topoisomerase inhibitors, and antimetabolites.

The present invention also relates to a method for the treatment of cancer, comprising administering to a patient a pharmaceutically active amount of at least one multi-targeting antifolate and a pharmaceutically active amount of THF, methylene-THF and/or methyl-THF. Preferably, at least 60% by weight of said THF, methyl-THF and/or methylene-THF is in the form of a biologically active isomer. The method may further comprise the administration of a chemotherapeutic agent selected from the group consisting of anthracyclines, platinum derivatives, topoisomerase inhibitors, and antimetabolites.

DETAILED DESCRIPTION OF THE INVENTION

Figure 1:
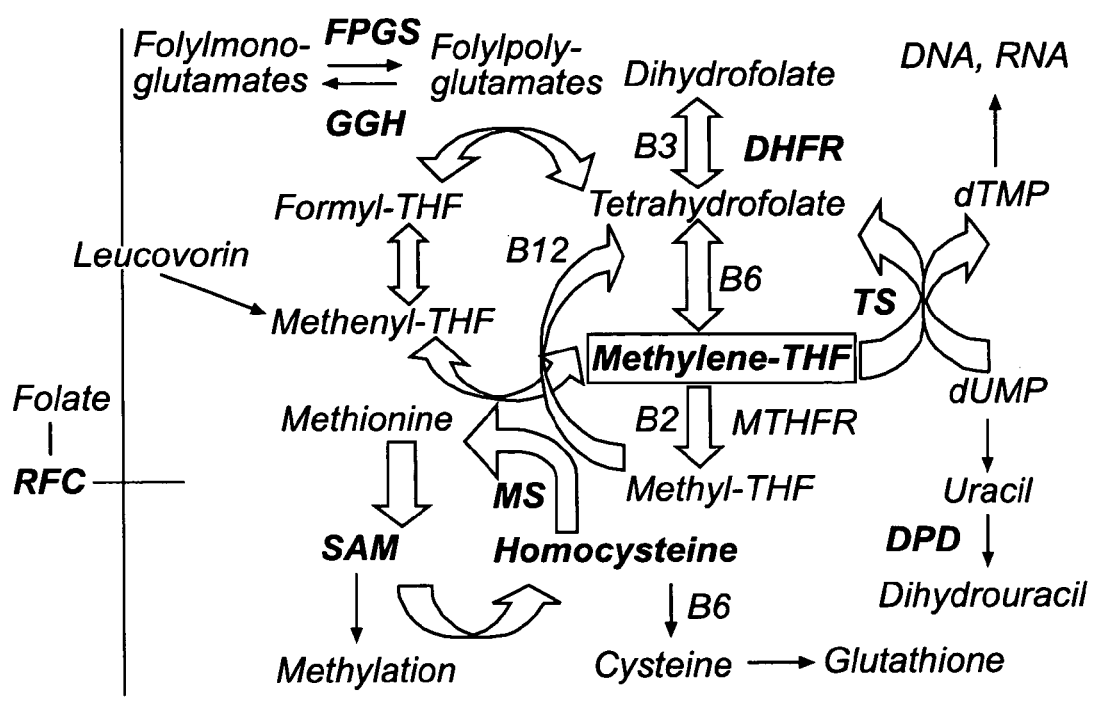
FIG. 1 shows the main metabolic pathways by which folate impact on DNA synthesis, repair and methylation.

In the research work leading to the present invention, the inventors surprisingly found that by co-administering THF, methylene-THF and/or methyl-THF, and multi-targeting antifolates, it is possible to remarkably reduce toxic side-effects of the multi-targeting antifolates without diminishing the anti-tumour action of the drugs.

The present inventors have shown (see example 2) that by combining a multi-targeting antifolate with the natural form of methylene-THF, the dose of the multi-targeting antifolate may be increased significantly without increasing toxicity.

Further, other chemotherapeutic agents, such as anthracyclines, platinum derivaties, topoisomerase inhibitors, and antimetabolites, may be administered in addition thereto, in order to further increase the cytotoxicity in the tumor while keeping the side-effects at a low level.

5,10-methylene-tetrahydrofolate (in the following referred to as methylene-THF, or $CH_2FH_4$) is a normal intracellular metabolite of folic acid, for use in thymidylate synthesis by thymidylate synthase (TS). The same is true with respect to the polyglutamates of methylene-THF. Methylene-THF is also used by several other enzymes including $CH_2FH_4$-reductase, serine hydroxymethylase and C1-tetrahydrofolate synthase and $CH_2FH_4$ dehydrogenase. These interconversions using methylene-THF are essential for purine synthesis, amino acid synthesis, and lipid metabolism. Thus, methylene-THF is located at a metabolic branch point as a substrate for at least 4 different enzymes (Spears et al; U.S. Pat. No. 5,376,658).

As stated above, previous studies have shown that folate status may modulate the toxicity and efficacy of cancer chemotherapy. The present inventors have found that the positive effect of folic acid is due to the increased level of methylene-THF that is formed from folic acid. Higher levels of methylene-THF in the cells leads to a more efficient TS-inhibition, which results in a thymidine-less state and increases uracil misincorporation in DNA.

Since methylene-THF is the active substance of folic acid metabolism, the use of this endogen folate for reducing toxicity in cancer treatment is much more favourable than the use of folic acid.

Dietary folates are a mixture of polyglutamated folates that are digested to monoglutamyl forms by the action of an enzyme anchored to the small intestinal brush border membrane and expressed by the glutamate carboxypeptidase II gene (GCPII) (Devlin A M et al, "Glutamate carboxypeptidase II: a polymorphism associated with lower levels of serum folate and hyperhomocysteinemia"; Hum Mol Genet 2000; 9:2837-44). After deconjugation in the small intestine, folic acid is reduced to tetrahydrofolate in the liver. Reduced folates are secreted into the small intestine with bile, where they are reabsorbed and distributed to other tissues.

The reduced folate carrier, RFC-1, is the major transporter of reduced folates into the cells (Sirotnak F M, Tolner B, "Carrier-mediated membrane transport of folates in mammalian cells"; Annu Rev Nutr 1999; 19:91-122). Intracellularly, reduced folate monoglutamates are converted to polyglutamates by the enzyme folylpolyglutamate synthase (FPGS) (Shane B, "Folylpolyglutamate synthesis and role in the regulation of one-carbon metabolism"; Vitam Horm 1989; 45:263-335). The polyglutamated form of tetrahydrofolate is then further converted to 5,10-methylenetetrahydrofolate (methylene-THF), required as a methyl donor in the conversion of dUMP to dTMP (Spears C P et al, "Deoxyuridylate effects on thymidylate synthase-5-fluorodeoxyuridylate-folate ternary complex formation"; Biochem Pharmacol 1989; 38:2985-93; Spears C P, et al "Thymidylate synthetase inhibition in malignant tumors and normal liver of patients given intravenous 5-fluorouracil", Cancer Res 1984; 44:4144-50). The conversion is catalysed by thymidylate synthase (TS). Methylene-THF is also the precursor of the metabolically active 5-methyltetrahydrofolate (methyl-THF), utilized in the remethylation of homocysteine. Conversion of methylene-THF to methyl-THF is dependent on the enzyme methylenetetrahydrofolate reductase (MTHFR).

The enzyme γ-glutamyl hydrolase (GGH) catalyzes the degradation of inter- and intracellular polyglutamates (Galivan J et al, "Glutamyl hydrolase pharmacological role and enzymatic characterization", Pharmacol Ther 2000; 85:207-15). FIG. 1 summarizes the main metabolic pathways by which folate and homocysteine impact on DNA synthesis, repair and methylation. The enzyme MTHFR balances the DNA methylation and DNA synthesis pathways to maintain normal homeostasis. (RFC=reduced folate carrier; FPGS=folylpolyglutamate synthase; GGH=γ-glutamyl hydrolase; TS=thymidylate synthase; THF=tetrahydrofolate; MTHFR=methylene-tetrahydrofolate reductase; MS=methionine synthase; SAM=S-adenosylmethionine; DPD=dihydro-pyrimidine dehydrogenase; B2=riboflavin; B6=pyridoxine; B12=cobalamin.)

As shown, proper functioning of the DNA synthesis and methylation pathways requires riboflavin (vitamin B2), pyridoxine (vitamin B6), and cobalamin (vitamin B12), in addition to folates. Inadequate levels of any of these metabolites will result in elevated homocysteine levels. Pyridoxine deficiency will also impair the cellular ability to produce glutathione, the master anti-oxidant needed for detoxification of free radicals and alkylating agent damage.

Oral folates are generally available in two supplemental forms, folic and folinic acid. The biochemical basis for modulation of fluorouracil (FU) activity by folic acid or folinic acid (leucovorin) is elevation of the metabolite methylene-THF, which stabilizes the inhibitory ternary complex formed between methylene-THF, thymidylate synthase and the active metabolite of 5-FU. Folinic acid is an immediate precursor of methylene-THF, since oral administration of folinic acid bypasses the deconjugation and reduction steps needed for folic acid. Folinic acid seems to be a more metabolically active form of folate than folic acid and, as a reduced folate, might directly cross the brain-blood barrier. Like folic acid, folinic acid must be methylated to be metabolically active. The methylation step of folic and folinic acid requires adequate levels of serine and a functional serine hydroxymethyltransferase (SHMT) enzyme (Costi M P, Ferrari S, "Update on antifolate drugs targets"; Curr Drug Targets 2001; 2:135-66). Supplementation with the reduced folates methylene-THF and methyl-THF has the advantage of bypassing this methylation step.

Pharmacogenetics aims to identify individuals predisposed to high risk of toxicity from conventional doses of cancer chemotherapeutic agents. Interindividual variability in the efficacy and toxicity of drug therapy is associated with polymorphisms in genes encoding drug-metabolizing enzymes, transporters, or drug targets.

The key metabolite methylene-THF is involved directly in biosynthesis of dTMP, in conversion to 10-formyl-THF for purine synthesis, and in reduction to methyl-THF for methylation of homocysteine to methionine (Kelly G S. Folates: supplemental forms and therapeutic applications. Altern Med Rev 1998; 3:208-20). The conversion of methylene-THF to methyl-THF requires the enzyme MTHFR.

Aberrations in the distribution of different folates may be caused by the MTHFR C677T polymorhism (Guinotte C L et al, "Methylenetetrahydro-folate reductase 677C→T variant modulates folate status response to controlled folate intakes in young women"; J Nutr 2003; 133:1272-80). Homo- or heterozygosity for the T allele results in a MTHFR enzyme with suboptimal activity and a raise in methylene-THF. A link between MTHFR polymorphism and tumor response to 5-FU was detected in a recent study by Cohen et al (Cohen V et al, "Methylenetetrahydrofolate Reductase Polymorphism in Advanced Colorectal Cancer: A Novel Genomic Predictor of Clinical Response to Fluoropyrimidine-based Chemotherapy"; Clin Cancer Res 2003; 9:1611-5). Patients with CT or TT genotype responded better to the therapy than patients with the CC genotype. The MTHFR C677T genotype may also be predictive of clinical toxicity to raltitrexed (Stevenson J P et al "Phase I clinical and pharmacogenetic trial of irinotecan and raltitrexed administered every 21 days to patients with cancer"; J Clin Oncol 2001; 19:4081-7). Homozygotes with the MTHFR C677T polymorphism experienced less raltitrexed-associated toxicity compared to those with wild-type or heterozygous genotypes.

Conversion of methylene-THF to methyl-THF may be impaired in individuals carrying a MTHFR enzyme with suboptimal activity (Guinotte C L et al "Methylenetetrahydrofolate reductase 677C→T variant modulates folate status response to controlled folate intakes in young women"; J Nutr 2003; 133:1272-80). Also, high levels of homocysteine or S-adenosylhomocysteine, as is found in folate deficient individuals, are known to inhibit the MTHFR enzyme (De Cabo S F et al, "Molecular and cytological evidence of S-adenosyl-L-homocysteine as an innocuous undermethylating agent in vivo"; Cytogenet Cell Genet 1995; 71:187-92). Thus, when choosing between methylene-THF and methyl-THF it might be important to take the patients genotype and folate status into consideration.

The X-ray repair cross-complementing gene I (XRCC1) protein has an important function in base excision repair of DNA. Different polymorphic forms of the protein exist, and the Arg399Gln polymorphism has been associated with risk of developing CRC as well as with resistance to oxaliplatin/5-FU chemotherapy (Stoehlmacher J et al, "A polymorphism of the XRCC1 gene predicts for response to platinum based treatment in advanced colorectal cancer" Anticancer Res 2001; 21:3075-9). Possibly, the XRCC1 gene may also be inactivated by aberrant methylation or by mutations caused by folate deficiency. Reversal of oxaliplatin resistance could be accomplished using folates like methylene-THF.

Further, low dietary intake or blood concentrations of folate are associated with an increased risk of colorectal neoplasia. In fact, epidemiologic studies have established an inverse association between folate status and colorectal neoplasia (Kim et al; "Colonic mucosal concentrations of folate correlate well with blood measurements of folate status in persons with colorectal polyps", Am J Clin Nutr 1998; 68: 866-72).

The use of THF, methylene-THF and/or methyl-THF for treatment of folate deficiency in colonic mucosa is very advantageous, since the most efficient folate is thereby administered directly to the site where it is needed the most.

Methylated folates may also reduce severe diarrhea induced by multi-targeting antifolates by protecting the neural network in the epithelial mucosa.

In connection to the present invention, natural as well as synthetic THF, methylene-THF and methyl-THF may be used. Further, prodrugs to THF, methylene-THF and/or methyl-THF may be used. THF, methylene-THF and methyl-THF may exist in several isomeric forms, however, the biologically active isomers of THF, methylene-THF and methyl-THF, respectively, are preferred according to the present invention. As used herein, "biologically active isomer" relates to an endogen isomer of THF, methylene-THF or methyl-THF, i.e. a natural form which fit into the enzyme systems in the body.

One natural, biologically active isomer of THF is [6S]-THF, one natural, biologically active isomer of methylene-THF is [6R]-methylene-THF, and one natural, biologically active isomer of methyl-THF is [6S]-methyl-THF.

The present inventors have surprisingly found that the biologically active isomers are most suitable to be used in combination with multi-targeting antifolates.

It has previously been shown that the natural isomer, i.e. the biologically active form, of methylene-THF (100% 6R-configuration) is a better growth factor than the racemic mixture (50% 6R-configuration and 50% 6S-configuration). One would therefore expect the natural isomer to be unfavourable to combine with a chemotherapeutic drug due to the risk for an excessive growth of the tumor. However, upon combination with a multi-targeting antifolate, the property of being a better growth factor is actually useful, because more cancer cells are then stimulated to enter the cell cycle. This is in this case advantageous, since the multi-targeting antifolates mainly affect cells during cell division.

According to the present invention, it is preferred that at least 60% by weight of the THF, methyl-THF and/or methylene-THF is in the form of a biologically active isomer. More preferably, at least 75% is in the form of a biologically active isomer, and most preferably, at least 95% is in the form of a biologically active isomer. The higher weight portion of a biologically active isomer, the better result will be achieved. This is the case for all embodiments of the invention.

THF, methylene-THF and methyl-THF for use according to the invention suitably has a purity of 90% or higher. A purity of 97% or higher is preferred. A higher purity provides for a better stability of the folates. At low purities, THF, methylene-THF and methyl-THF are very susceptible to oxidation, and thus unstable.

Alternative expressions for methylene-THF are 5,10-methylene-THF, or $5,10\text{-}CH_2\text{---}FH_4$. Methylene-THF may e.g. be used in the form of its Ca or $Na_2$ salt, or in the form of various sulfate salts. Further, according to the present invention, the free acid may be used, i.e. methylene-tetrahydrofolic acid, or 5,10-methylenetetrahydropteroyl-glutamic acid $(5,10\text{-}CH_2\text{---}H_4\text{---}PteGlu)$.

Alternative expressions for methyl-THF are 5-methyl-THF, or $5\text{-}CH_3\text{---}H_4F$. Methyl-THF may e.g. be used in the form of its Ca or $Na_2$ salt, or in the form of various sulfate salts. Further, according to the present invention, the free acid may be used, i.e. methyl-tetrahydrofolic acid, or methyltetrahydropteroyl-glutamic acid $(5\text{-}CH_3\text{---}H_4PteGlu)$.

Alternative expressions for THF are $H_4F$, or 5,6,7,8-tetrahydrofolate. THF may e.g. be used in the form of its Ca or $Na_2$ salt, or in the form of various sulfate salts. Further, according to the present invention, the free acid may be used, i.e. tetrahydrofolic acid, or tetrahydropteroyl-glutamic acid $(H_4PteGlu)$.

The term "chemotherapeutic agent" as used herein relates to a medicament for the treatment of cancer.

The term "multi-targeting antifolate" (or "multi-functional antifolate") as used herein relates to an antifolate which acts on two or more of the enzymes involved in folate synthesis. The difference between single enzyme targeting antifolates and multi-targeting antifolates is illustrated in "Pemetrexed Disodium: A Novel Antifolate Clinically Active Against Multiple Solid Tumors" by Hanauske A, et al, where the inhibitory activity of pemetrexed and MTX against different enzymes is compared. Pemetrexed demonstrate significant inhibitory activity for multiple enzyme systems, unlike MTX.

Further, the multifunctionality of the multi-targeting antifolates decreases the risk for the development of drug resistance, which is a great difference compared to single enzyme targeting antifolates.

The multi-targeting antifolate may for example be selected from the group consisting of pemetrexed (trade name: Alimta®), raltitrexed (trade name: Tomudex®), and lometrexol. (The multifunctionality of raltitrexed is shown e.g. by Jackman A L et al in "ICI D 1694, a quinazoline antifolate thymidylate synthase inhibitor that is a potent inhibitor of L1210 tumor cell growth in vitro and in vivo: a new agent for clinical study", Cancer Res 1991 October 15; 51(20):5579-86.)

The terms "anthracycline", "platinum derivative", "topoisomerase inhibitor", and "antimetabolite" as used herein relates to these compounds as defined in the National Library of Medicine.

The term "patient" as used herein relates to any human or non-human mammal in need of being treated with the methods, kit or pharmaceutical compositions according to the invention.

The term "treatment" as used herein relates to both treatment in order to cure or alleviate the symptoms of different types of cancer, and to treatment in order to prevent the development of cancer. In particular, solid tumors are well suited to be treated according to the invention.

The term "pharmaceutically active amount" as used herein relates to a dose of a substance that will lead to the desired pharmacological and/or therapeutic effect. The desired pharmacological and/or therapeutic effect is, as stated above, to cure or alleviate the symptoms of different types of cancer, and to prevent the development of cancer.

THF, methylene-THF and/or methyl-THF, and the multi-targeting antifolate, may be administered simultaneously or consequtively. When administered consequtively, either THF, methylene-THF and/or methyl-THF is administered first and thereafter the multi-targeting antifolate, or the multi-targeting antifolate is administered first and thereafter THF, methylene-THF and/or methyl-THF. The interval between the administrations depends on the drug characteristics, and may e.g. vary from hours to days. However, shorter and longer intervals may be used.

In case other chemotherapeutic agents, i.e. anthracyclines, platinum derivatives, topoisomerase inhibitors, and antimetabolites, are to be administered as well, they may be administered either simultaneously with THF, methylene-THF and/or methyl-THF, or simultaneously with the multi-functional antifolate. Further, all substances, i.e. THF, methylene-THF and/or methyl-THF, the multi-targeting antifolate, and other chemotherapeutic substances may be administered simultaneously. The other chemotherapeutic agents may also be administered separate from THF, methylene-THF and/or methyl-THF, and the multi-targeting antifolate.

The order in which drugs and folate are administered could be of major importance for the outcome of chemotherapeutic treatment. As an illustration, Raghunathan et al., showed that tumor growth was suppressed approximately 80% when 5-FU was administered to folate depleted animals 1 hr after folinic acid administration, compared with approximately 50% suppression in control mice (Raghunathan K et al "Impact of schedule on leucovorin potentiation of fluorouracil antitumor activity in dietary folic acid deplete mice"; Biochem Pharmacol 1997; 53:1197-202). Folinic acid administered 12 hr before 5-FU resulted in tumor growth stimulation that was consistent with the pronounced growth stimulation when folinic acid was administered without 5-FU.

The pharmaceutical compositions according to the invention may also comprise other substances, such as an inert vehicle, or pharmaceutical acceptable adjuvants, carriers, preservatives, ascorbic acid, ascorbate, antioxidants, etc, which are well known to persons skilled in the art.

The pharmaceutical compositions according to the invention may be formulated by conventional manufacturing methods, such as e.g. by manufacturing methods similar to those used for the production of leucovorin.

Examples of cancers to be treated according to the invention are breast cancer, gastric cancer, gall bladder cancer, bile duct cancer, colon cancer, rectal cancer, liver cancer, pancreatic cancer, head and neck cancer, and mesotheolioma cancer.

THF, methylene-THF and/or methyl-THF is preferably administered in a dose of 100 μg to 1000 mg, preferably a dose of 100-200 mg, corresponding to approximately 1-5 mg/kg body weight. The dose will be adjusted individually, and may thus vary, e.g. depending on the condition of the patient.

The dose may be administered e.g. daily, weekly, or monthly. It may, for example, be administered subcutaneously, intramuscularely, intravenously, intraarterially, intraperitoneally, intranasally or orally.

Furthermore, it is possible to combine the treatment according to the invention with other conventional pharmacological treatments of cancer. THF, methylene-THF and/or methyl-THF and the multi-targeting antifolate may thus be administered in combination with other conventional pharmaceuticals used to treat cancer.

The compositions according to the invention may also be co-administered with vitamin B12, vitamin B6, and vitamin B2.

Examples of combinations of multi-targeting antifolates and THF, methylene-THF and/or methyl-THF are:
Pemetrexed+THF, methylene-THF and/or methyl-THF
Pemetrexed+5-fluorouracil+THF, methylene-THF and/or methyl-THF
Raltitrexed+THF, methylene-THF and/or methyl-THF
Raltitrexed+5-fluorouracil+THF, methylene-THF and/or methyl-THF.

EXAMPLES

The invention will now be further explained in the following examples. These examples are only intended to illustrate the invention and should in no way be considered to limit the scope of the invention.

Example 1

Administration of Methylene-THF Vs Administration of Folinic Acid

The level of increase of tissue concentration of methylene-THF after administration of leucovorin and methylene-THF, respectively, has been compared.

Figure 2:
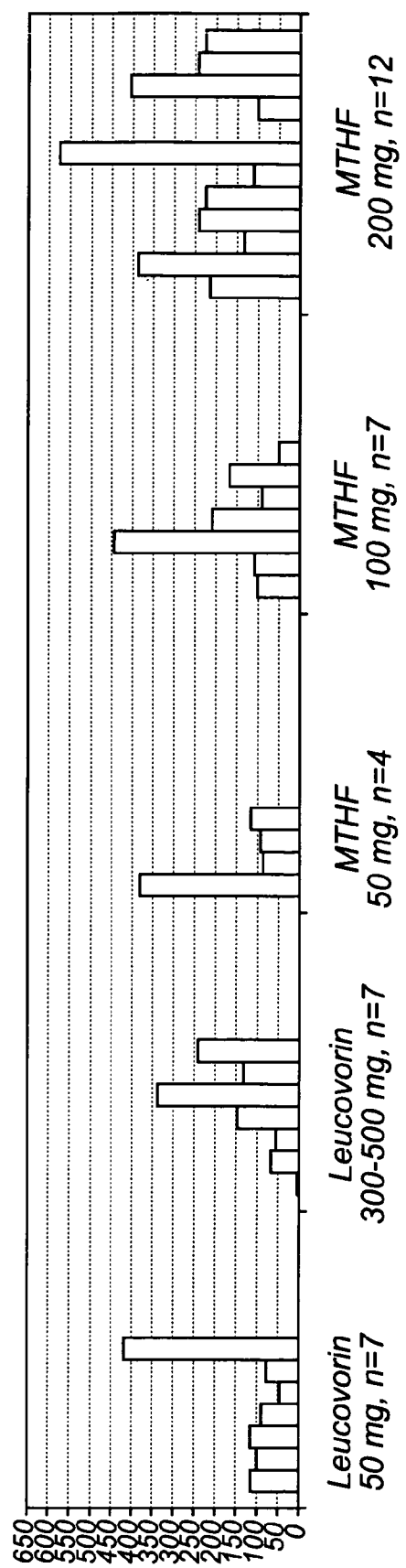
FIG. 2 shows the percent increase of tissue concentration of methylenetetrahydrofolate (MTHF) in liver metastases from colorectal cancer in individual patients.
Figure 3:
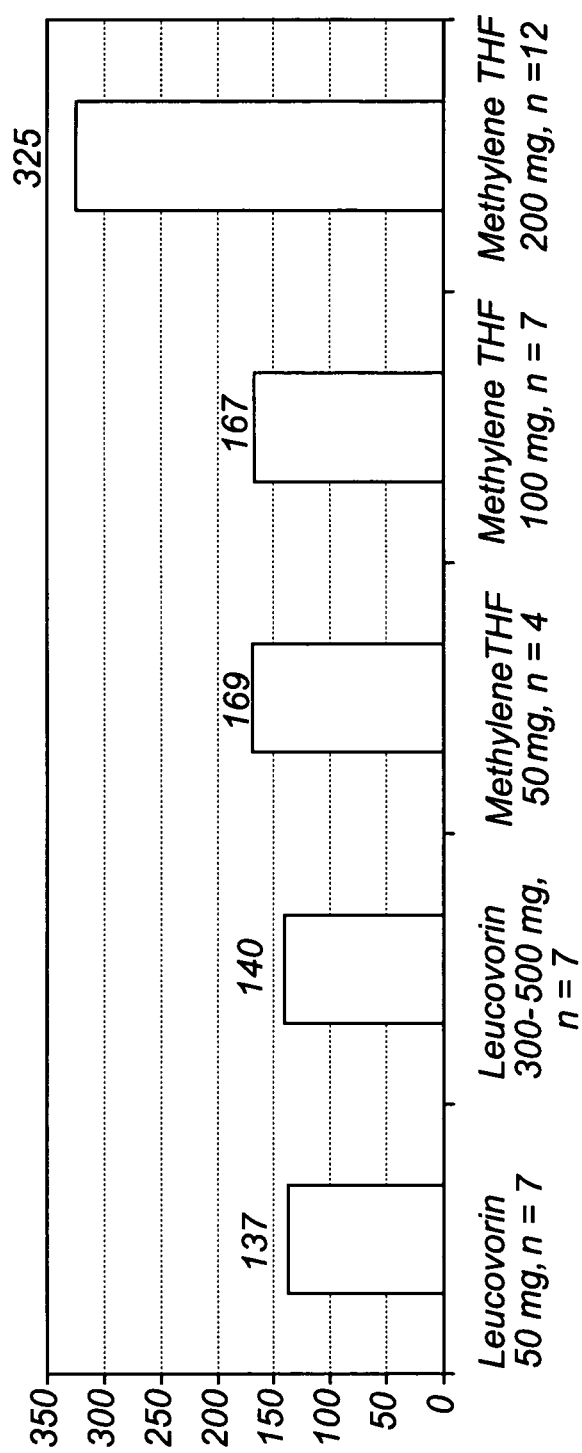
FIG. 3 shows the mean percent increase of tissue concentration of methylenetetrahydrofolate (MTHF) in liver metastases from colorectal cancer in individual patients.

Patients operated upon due to liver metastases were given a dose of folates. Biopses were taken from the tumor before i.v. bolus injection of leucovorin on methylenetetrahydrofolate. At 20 minutes a new tumor biopsy was taken and the concentration of MTHF was assayed. The administration of methylene-THF led to a greater tissue concentration of methylene-THF than leucovorin. The results are shown in FIGS. 2 and 3. These results indicate that administration of methylene-THF instead of folinic acid is more efficient.

Example 2

Multi-Targeting Antifolate Therapy (ALIMTA) in Combination with the Natural Isomer of Methylenetetrahydrofolate (R-5,10-CH$_2$FH$_4$) in an Experimental Adenocarcinoma in Rats Method The following experimental study was approved by the local ethical committee at the Göteborg University.

Eight inbred female Wistar rats were during general anesthesia inoculated in the central liver lobe with 0.1 ml of 1.0 million viable tumor cells of an experimental adenocarcinoma. On day 5 the animals were relaparotomized during general anesthesia, the body weight was recorded and the size of the solitary liver tumor was measured with vernier calipers.

The animals were randomly allocated to two groups. Group 1 received intravenous injections of ALIMTA (pemetrexed) 0.01 mg/kg and group 2 received 0.1 mg/kg of ALIMTA. Both groups received 15 mg/kg of R-5,10-CH$_2$FH$_4$ immediately following the injections of ALIMTA. Therapy was administered through intravenous injections via the tail vein on days 6-8 and days 11-12. On day 13 all animals were sacrificed by an overdose of anesthesia.

The body weights were recorded and the size of the liver tumors was measured. The wet weights of the excised liver tumor and spleen were recorded.

Results

Figure 4:
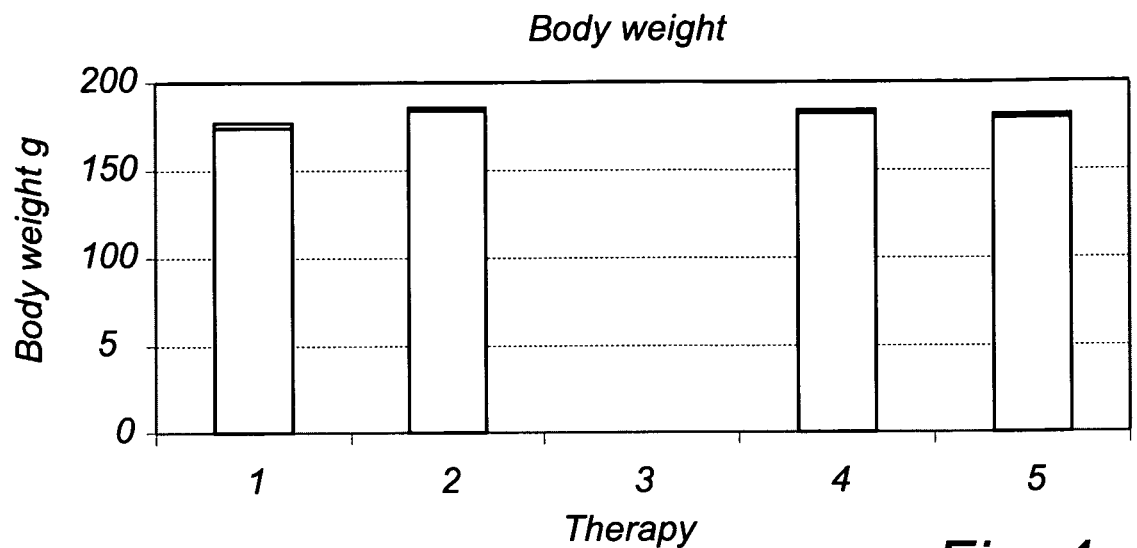
FIG. 4 shows the body weights at day 5 and 13 (mean±SEM) of the animals in example 2.

All animals survived the experimental period and no signs of toxicity were observed. The body weights on day 5 and 13 are shown in FIG. 4. (FIG. 4 shows the body weights at day 5 and 13. Group 1 (day 5=1 and day 13=2) and group 2 (day 5=4 and day 13=5). Mean±SEM.)

Figure 5:
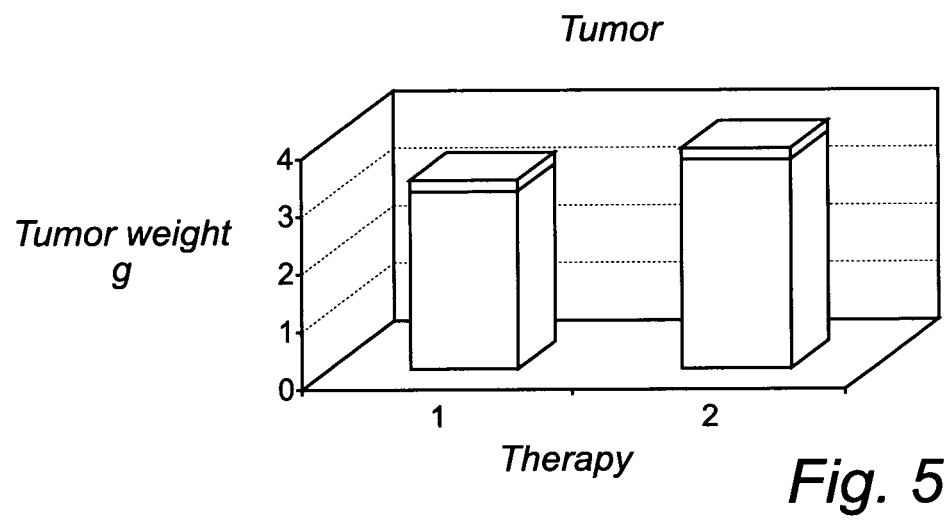
FIG. 5 shows the tumor weights of the liver tumors (mean±SEM) of the animals in example 2.

All animals receiving 0.01 mg/kg of ALIMTA were found with extrahepatic tumor growth in the abdominal cavity as metastases to the lungs. The tumor weights of the liver tumors in both groups are shown in FIG. 5. The total tumor weights of extrahepatic tumor growth in the abdominal cavity and lung metastases were not recorded. Only liver tumor weights are shown in FIG. 5. (FIG. 5 shows the tumor weights of the liver tumors in group 1 (1) and group 2 (2). Mean±SEM.)

Figure 6:
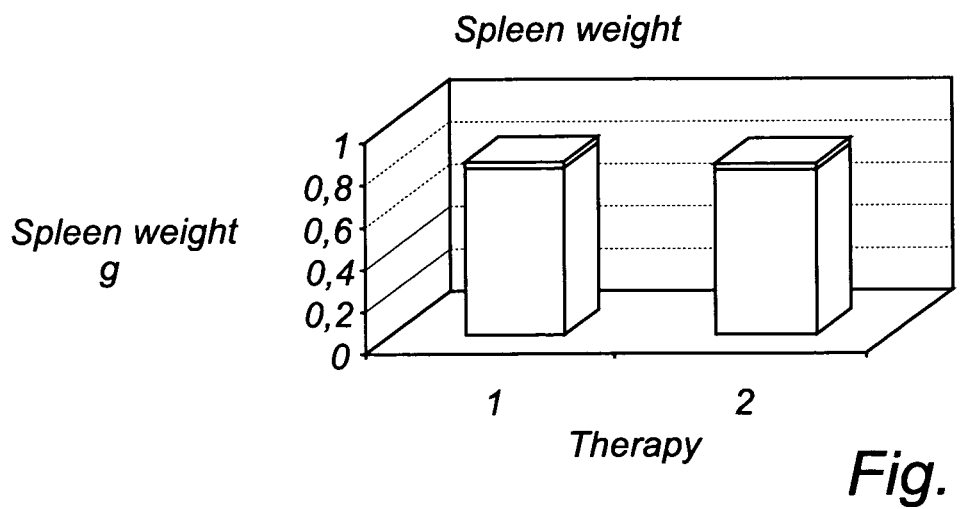
FIG. 6 shows the spleen weights (mean±SEM) of the animals in example 2.

The wet weights of the spleen in the two groups are shown in FIG. 6. (FIG. 6 shows the spleen weights in group 1 (1) and group 2 (2). Mean±SEM.) It is well known in the art that the toxicity of a drug can be monitored by looking at the spleen weight as a surrogate marker.

Conclusion

This experiment is a proof for the principle that it is possible to combine a multifunctional antifolate with the natural form of methylenetetrahydrofolate, and that such combination can improve the antitumour effect. In the group with the highest Alimta dose, no extrahepatic metastasies were recorded, and still no general toxicity could be seen.

Example 3

The Effect of a Multi-Targeting Antifolate

Figure 7:
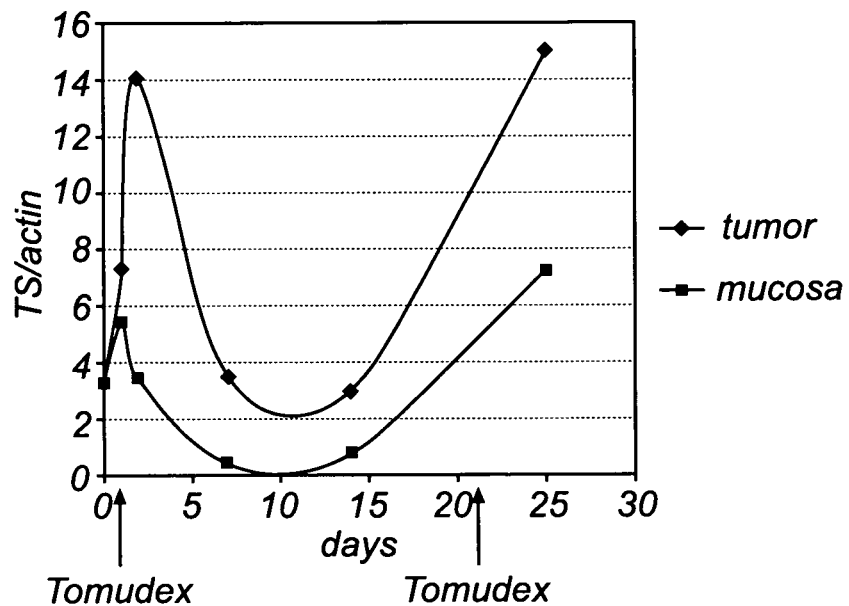
FIG. 7 shows the TS expression levels after intravenous bolus injection of a multi-targeting antifolate.
Figure 8:
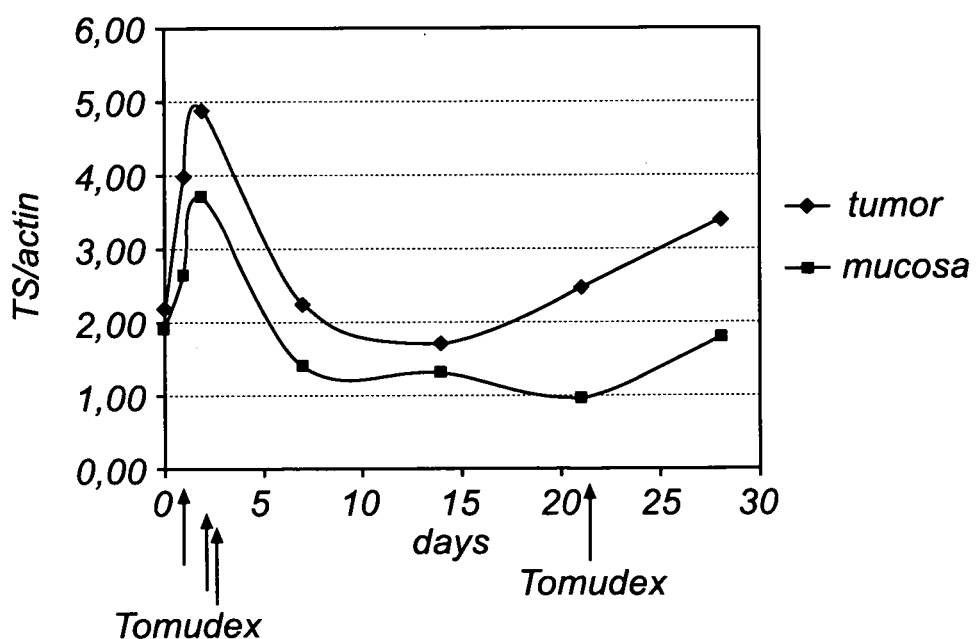
FIG. 8 shows the mean gene expression levels of TS after intravenous bolus injection of a multi-targeting antifolate.

In this experiment, the effect of a multi-targeting antifolate, i.e. Tomudex (raltitrexed), was shown. FIG. 7 shows the TS expression levels in the tumor after Tomudex intravenous bolus injection, and FIG. 8 shows the gene expression levels of TS after Tomudex intravenous bolus injection.

Nine colorectal cancer patients were included in the study, and the expression levels were measured in actin, which is a protein serving as an important structural molecule for the cytoskeletons of many eukaryotic cells.

This experiment shows that by using a multi-targeting antifolate only, the normal mucosa is actually more adversely affected than the tumor. This also corresponds to the clinical findings; severe toxic effects from the bowel made it impossible to continue the treatment.

Thus, the effects obtained by the present invention, i.e. the reduction of the toxicity of multi-functional antifolates while maintaining the cytotoxic effect, are very much sought after.

While the invention has been described in detail and with reference to specific embodiments thereof, it will be apparent for one skilled in the art that various changes and modifications can be made therein without departing from the spirit and scope thereof.

The invention claimed is:

1. A pharmaceutical composition comprising [6R]-methylene-tetrahydrofolate and at least one multi-targeting antifolate, wherein at least 60% by weight of methylene-tetrahydrofolate in the composition is [6R]-methylene-tetrahydrofolate.

2. The pharmaceutical composition according to claim 1, wherein said multi-targeting antifolate is selected from the group consisting of pemetrexed, raltitrexed, and lometrexol.

3. The pharmaceutical composition according to claim 1, further comprising at least one chemotherapeutic agent selected from the group consisting of an anthracycline, a platinum derivative, a topoisomerase inhibitor, and an antimetabolite.

4. The pharmaceutical composition according to claim 1, wherein said [6R]-methylene-tetrahydrofolate and said at least one multi-targeting antifolate, are formulated in separate pharmaceutical compositions.

5. The pharmaceutical composition according to claim 1, wherein said [6R]-methylene-tetrahydrofolate and said at least one multi-targeting antifolate, are formulated in a common pharmaceutical composition.

6. A kit comprising a pharmaceutical composition comprising [6R]-methylene-tetrahydrofolate and a pharmaceutical composition comprising at least one multi-targeting antifolate, wherein at least 60% by weight of methylene-tetrahydrofolate in the composition is [6R]-methylene-tetrahydrofolate.

7. The kit according to claim 6, further comprising a pharmaceutical composition comprising at least one chemotherapeutic agent selected from the group consisting of an anthracycline, a platinum derivative, a topoisomerase inhibitor, and an antimetabolite.

8. A method of reducing toxicity resulting from multi-targeting antifolate chemotherapy, the method comprising administering to a patient in need thereof a pharmaceutically active amount of [6R]-methylene-tetrahydrofolate and a pharmaceutically active amount of at least one multi-targeting antifolate, wherein at least 60% by weight of methylene-tetrahydrofolate administered is [6R]-methylene-tetrahydrofolate.

9. The method according to claim 8, wherein said multi-targeting antifolate is selected from the group consisting of pemetrexed, raltitrexed, and lometrexol.

10. The method according to claim 8, further comprising administering a pharmaceutically active amount of a chemotherapeutic agent selected from the group consisting of an anthracycline, a platinum derivative, a topoisomerase inhibitor, and an antimetabolite.

11. The method according to claim 8, wherein said [6R]-methylene-tetrahydrofolate and said at least one multi-targeting antifolate, are administered consecutively.

12. The method according to claim 8, wherein said [6R]-methylene-tetrahydrofolate and said at least one multi-targeting antifolate, are administered simultaneously.

13. The method according to claim 8, wherein said cancer is selected from the group consisting of breast cancer, gastric cancer, gall bladder cancer, bile duct cancer, colon cancer, rectal cancer, liver cancer, pancreatic cancer, head and neck cancer, and mesothelioma cancer.

14. The pharmaceutical composition according to claim 1, wherein at least 75% by weight of the methylene-tetrahydrofolate is [6R]-methylene-tetrahydrofolate.

15. The pharmaceutical composition according to claim 14, wherein at least 95% by weight of the methylene-tetrahydrofolate is [6R]-methylene-tetrahydrofolate.

16. The method according to claim 8, wherein the pharmaceutically active amount of [6R]-methylene-tetrahydrofolate comprises at least 15 mg per kilogram of patient body mass.

* * * * *